United States Patent
Hess et al.

(10) Patent No.: US 10,401,305 B2
(45) Date of Patent: Sep. 3, 2019

(54) TIME-VARYING INTENSITY MAP GENERATION FOR RETICLES

(71) Applicant: KLA-Tencor Corporation, Milpitas, CA (US)

(72) Inventors: Carl E. Hess, Los Altos, CA (US); Rui-fang Shi, Cupertino, CA (US); Thomas Vavul, San Francisco, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 770 days.

(21) Appl. No.: 13/757,103

(22) Filed: Feb. 1, 2013

(65) Prior Publication Data
US 2013/0211736 A1    Aug. 15, 2013

Related U.S. Application Data

(60) Provisional application No. 61/599,301, filed on Feb. 15, 2012.

(51) Int. Cl.
*G03F 1/84* (2012.01)
*G01N 21/95* (2006.01)
(Continued)

(52) U.S. Cl.
CPC ....... *G01N 21/95* (2013.01); *G01N 21/95607* (2013.01); *G03F 1/84* (2013.01);
(Continued)

(58) Field of Classification Search
CPC ........ G01N 21/95676; G01N 21/95607; G03F 7/7065; G03F 7/705; G03F 1/62–88; G06T 7/001; G06T 7/0002; G06T 7/00097

See application file for complete search history.

(56) References Cited

U.S. PATENT DOCUMENTS 6,614,520 B1 *   9/2003   Bareket .......... G01N 21/95607
                                              356/237.3
7,069,155 B1     6/2006   Phan et al.
                          (Continued)

FOREIGN PATENT DOCUMENTS

CN      101295130 A    10/2008
JP       06174652 A     6/1994
                (Continued)

OTHER PUBLICATIONS

"International Application Serial No. PCT/US2013/074841, Search Report and Written Opinion dated Sep. 25, 2014", 12 pgs.
(Continued)

*Primary Examiner* — Mohamed Charioui
*Assistant Examiner* — Christine Y Liao
(74) *Attorney, Agent, or Firm* — Kwan & Olynick LLP

(57) ABSTRACT

An optical reticle inspection tool is used during a first inspection to obtain, for each set of one or more patch areas of the reticle, a reference average of multiple reference intensity values corresponding to light measured from sub-areas of each patch area. After using the reticle in photolithography processes, the optical reticle inspection tool is used during a second inspection to obtain, for each set of one or more patch areas, an average of multiple test intensity values corresponding to light measured from the sub-areas. The first and second inspections use the same tool setup recipe. A difference intensity map is generated, and such map comprises map values that each corresponds to a difference between each average of the test and reference intensity values for each set of one or more patches. The difference intensity map indicates whether the reticle has degraded over time more than a predefined level.

28 Claims, 8 Drawing Sheets

(51) Int. Cl.
*G01N 21/956* (2006.01)
*G03F 7/20* (2006.01)

(52) U.S. Cl.
CPC . *G03F 7/7065* (2013.01); *G01N 2021/95676* (2013.01); *G03F 7/705* (2013.01)

(56) References Cited

U.S. PATENT DOCUMENTS

| | | | |
|---|---|---|---|
| 7,564,545 | B2 | 7/2009 | Stokowski |
| 7,853,920 | B2 | 12/2010 | Preil et al. |
| 8,421,026 | B2 | 4/2013 | Ben-Zvi et al. |
| 8,855,400 | B2 | 10/2014 | Wang et al. |
| 2002/0085297 | A1 | 7/2002 | Boettiger et al. |
| 2003/0174876 | A1* | 9/2003 | Eran .......... G03F 1/84 382/144 |
| 2004/0240723 | A1 | 12/2004 | Sakai et al. |
| 2005/0004774 | A1* | 1/2005 | Volk .......... G01N 21/9501 702/108 |
| 2005/0166171 | A1 | 7/2005 | Bartov |
| 2005/0174570 | A1 | 8/2005 | Kvamme et al. |
| 2006/0038987 | A1 | 2/2006 | Maeda et al. |
| 2008/0052021 | A1 | 2/2008 | Morinaga et al. |
| 2008/0170773 | A1 | 7/2008 | Wihl et al. |
| 2008/0304056 | A1 | 12/2008 | Alles et al. |
| 2009/0037134 | A1 | 2/2009 | Kulkarni et al. |
| 2009/0136116 | A1* | 5/2009 | Okai .......... G06K 9/00 382/144 |
| 2009/0226076 | A1 | 9/2009 | Sakai et al. |
| 2011/0014577 | A1* | 1/2011 | Hashimoto .......... G01N 21/94 430/325 |
| 2011/0101226 | A1 | 5/2011 | Ben-Zvi et al. |
| 2011/0235905 | A1* | 9/2011 | Yokokawa .......... H04N 1/40068 382/165 |
| 2012/0002860 | A1 | 1/2012 | Sakai et al. |
| 2012/0005634 | A1* | 1/2012 | Seltmann .......... G03F 1/70 716/53 |
| 2013/0211736 | A1 | 8/2013 | Hess et al. |
| 2014/0168418 | A1 | 6/2014 | Hess |

FOREIGN PATENT DOCUMENTS

| | | |
|---|---|---|
| JP | H09198515 A | 7/1997 |
| JP | S6345541 A | 2/1998 |
| JP | 2004271421 | 9/2004 |
| JP | 2006018054 | 1/2006 |
| JP | 2006080437 | 3/2006 |
| JP | 2009521708 A | 6/2009 |
| JP | 2010224114 A | 10/2010 |
| JP | 2010533309 A | 10/2010 |
| JP | 2012002731 A | 1/2012 |
| KR | 1020100069503 A | 6/2010 |
| TW | 201131614 A | 9/2011 |
| WO | 0066549 A2 | 11/2000 |
| WO | 2006089630 A1 | 8/2006 |
| WO | 2009007977 A2 | 1/2009 |
| WO | 2011035946 | 3/2011 |
| WO | WO 11142196 A1 * | 11/2011 |
| WO | 2012012265 A2 | 1/2012 |
| WO | 2013142079 A1 | 9/2013 |

OTHER PUBLICATIONS

"Int'l Application Serial No. PCT/US2013/029587, Preliminary Report on Patentability dated Oct. 2, 2014", 8 pgs.
"Int'l Application Serial No. PCT/US2013/029587, Search Report and Written Opinion dated Jun. 24, 2013", 3 pgs.
"International Application Serial No. PCT/US2013/026224, Search Report and Written Opinion dated Jun. 3, 2013", 11 pgs.
Sagiv, Amir et al., "IntenCD: Mask Critical Dimension Variation Mapping", Proc. of SPIE vol. 7028, 70282X, Retrieved from the Internet: < http://proceedings.spiedigitallibrary.org/ on Jan. 14, 2013 Terms of Use: http://spiedl.org/terms >, Accessed on Jan. 14, 2013, 2008, 12 pgs.
"Chinese Application Serial No. 201380018790.X, Office Action dated Mar. 29, 2016", 19 pgs.
"International Application Serial No. PCT/US2015/022340, Search Report", 2 pgs.
"Japanese Application Serial No. 2014-557786, Office Action dated Oct. 6, 2016", 8 pgs.
"Taiwan Application Serial No. 102105191, Office Action dated Aug. 9, 2016", 8 pgs.
"U.S. Appl. No. 13/757,103, Final Office Action dated Jul. 14, 2016", 35 pages.
"U.S. Appl. No. 13/757,103, Non Final Office Action dated Jan. 27, 2017", 34 pages.
"U.S. Appl. No. 13/757,103, Non Final Office Action dated Dec. 21, 2015", 26 pgs.
"U.S. Appl. No. 14/664,565, Notice of Allowance dated Jun. 8, 2017", 9 pages.
"JP Office Action Pat. Ser. No. 2014-557786—Translation", dated Jun. 6, 2017.
"U.S. Appl. No. 14/664,565, Non Final Office Action dated Jan. 18, 2017", 12 pages.
"Chinese Application Serial No. 201380018790.X, Office Action dated Nov. 17, 2016", 17 pages.

* cited by examiner

TIME-VARYING INTENSITY MAP GENERATION FOR RETICLES

CROSS-REFERENCE TO RELATED APPLICATIONS

This application claims priority under 35 U.S.C. § 119 of prior U.S. Provisional Application No. 61/599,301, filed Feb. 15, 2012, titled "Time-Varying Intensity Map Measurement" by Carl E. Hess et al., which application is herein incorporated by reference in its entirety for all purposes.

TECHNICAL FIELD OF THE INVENTION

The invention generally relates to the field of reticle inspection. More particularly the present invention relates to a method to detect reticle degradation.

BACKGROUND

Generally, the industry of semiconductor manufacturing involves highly complex techniques for fabricating integrating circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are becoming increasingly smaller. The device is fault free prior to shipment to the end users or customers.

An integrated circuit is typically fabricated from a plurality of reticles. Generation of reticles and subsequent optical inspection of such reticles have become standard steps in the production of semiconductors. Initially, circuit designers provide circuit pattern data, which describes a particular integrated circuit (IC) design, to a reticle production system, or reticle writer. The circuit pattern data is typically in the form of a representational layout of the physical layers of the fabricated IC device. The representational layout includes a representational layer for each physical layer of the IC device (e.g., gate oxide, polysilicon, metallization, etc.), wherein each representational layer is composed of a plurality of polygons that define a layer's patterning of the particular IC device.

The reticle writer uses the circuit pattern data to write (e.g., typically, an electron beam writer or laser scanner is used to expose a reticle pattern) a plurality of reticles that will later be used to fabricate the particular IC design. A reticle inspection system may then inspect the reticle for defects that may have occurred during the production of the reticles.

A reticle or photomask is an optical element containing at least transparent and opaque regions, and sometimes semi-transparent and phase shifting regions, which together define the pattern of coplanar features in an electronic device such as an integrated circuit. Reticles are used during photolithography to define specified regions of a semiconductor wafer for etching, ion implantation, or other fabrication processes.

After fabrication of each reticle or group of reticles, each new reticle typically is free of defects or degradation. However, the reticle may become defective after use. Thus, there is a continuing need for improved reticle inspection techniques.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, a method of inspecting a photolithographic reticle is disclosed. A plurality of patch areas of a reticle is defined. Prior to using a reticle in any photolithography process, an optical reticle inspection tool is used during a first inspection to obtain, for each of a plurality of sets of one or more patch areas, a reference average of multiple reference intensity values corresponding to light measured from a plurality of sub-areas of each patch area of the reticle. After using the reticle in a plurality of photolithography processes, the optical reticle inspection tool is used during a second inspection to obtain, for each of the sets of one or more patch areas, an average of multiple test intensity values corresponding to light measured from the plurality of sub-areas of each patch area of the reticle. The same setup recipe for the optical reticle inspection tool is used for both the first and second inspections. A difference intensity map is generated, and such map comprises a plurality of map values that each corresponds to a difference between each average of the test intensity values and average of the reference intensity values for each of the sets of one or more patches. The difference intensity map indicates whether the reticle has degraded over time more than a predefined level.

In a specific implementation, the plurality of patch areas substantially comprises the entire active area of the reticle, and the difference intensity map is generated for the entire active area of the reticle. In another embodiment, the first and second inspections are performed while a pellicle is mounted on the reticle and the difference intensity map indicates whether a pellicle of the reticle has degraded over time more than a predefined level. In another aspect, the difference intensity map indicates that the reticle has degraded in a spatially radial pattern over time more than a predefined level. In one example implementation, each of the sets of one or more patch areas consists of a single patch area. In another example, each of the sets of one or more patch areas includes two or more of the patch areas.

In another embodiment, the method includes removing a global offset from the difference intensity map. In a further aspect, the difference intensity map comprises differently colored areas that correspond to different areas of the reticle that resulted in different changes in average intensity values between the first and second inspections. In yet another embodiment, the difference intensity map is generated to be normalized to a zero average. In one specific implementation, the difference intensity map is generated based on both reflected and transmitted light that is collected during the first and second inspections. In another aspect, the first inspection is performed prior to using the reticle in any photolithography process after such reticle has been verified as having minimal degradation.

In a further embodiment, the method includes repeating the operations for obtaining a second reference average for each of the sets of patch areas after the reticle has been cleaned, obtaining a second test average for each of the sets of patch areas after using the cleaned reticle in a second plurality of photolithography processes, and generating a second difference map based on the second reference and test average for each of the sets of one or more patch areas. In another aspect, the method further includes determining a global CD change based on a global offset in the difference intensity map. In yet another example, the difference intensity map is generated to account for pattern density dependencies.

In certain embodiments, the invention pertains to a system for inspecting a photolithographic reticle. The system includes at least one memory and at least one processor that are configured to perform at least some of the above described operations. In other embodiments, the invention pertains to computer readable media having instructions stored thereon for performing at least some of the above described operations.

These and other aspects of the invention are described further below with reference to the figures.

DETAILED DESCRIPTION OF EXAMPLE EMBODIMENTS

Figure 1A:
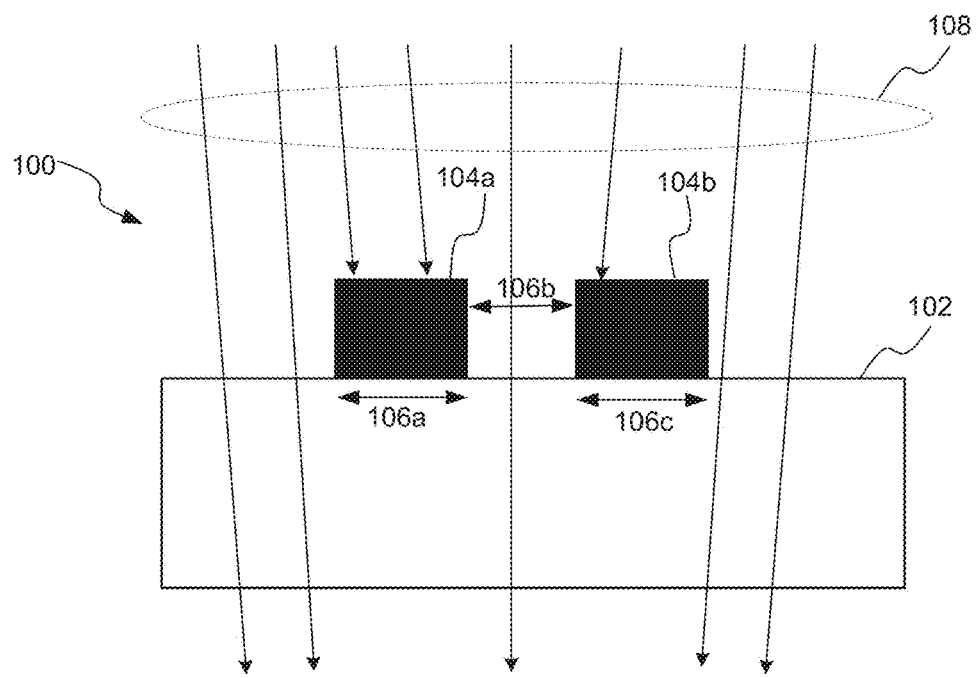
FIG. 1A is a diagrammatic side view of a reticle portion undergoing photolithographic exposure using a high power, deep ultra violet (UV) light.

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

The terms "reticle" generally includes a transparent substrate, such as glass, borosilicate glass, quartz, or fused silica having a layer of opaque material formed thereon. The opaque (or substantially opaque) material may include any suitable material that completely or partially blocks photolithographic light (e.g., deep UV). Example materials include chrome, molybdenum silicide (MoSi), tantalum silicide, tungsten silicide, opaque MoSi on glass (OMOG), etc. A polysilicon film may also be added between the opaque layer and transparent substrate to improve adhesion. A low reflective film, such as molybdenum oxide ($MoO_2$), tungsten oxide ($WO_2$), titanium oxide ($TiO_2$), or chromium oxide ($CrO_2$) may be formed over the opaque material.

The term reticle refers to different types of reticles including, but not limited to, a clear-field reticle, a dark-field reticle, a binary reticle, a phase-shift mask (PSM), an alternating PSM, an attenuated or halftone PSM, a ternary attenuated PSM, and a chromeless phase lithography PSM. A clear-field reticle has field or background areas that are transparent, and a dark-field reticle has field or background areas that are opaque. A binary reticle is a reticle having patterned areas that are either transparent or opaque. For example, a photomask made from a transparent fused silica blank with a pattern defined by a chrome metal adsorbing film can be used. Binary reticles are different from phase-shift masks (PSM), one type of which may include films that only partially transmit light, and these reticles may be commonly referred to as halftone or embedded phase-shift masks (EPSMs). If a phase-shifting material is placed on alternating clear spaces of a reticle, the reticle is referred to as an alternating PSM, an ALT PSM, or a Levenson PSM. One type of phase-shifting material that is applied to arbitrary layout patterns is referred to as an attenuated or halftone PSM, which may be fabricated by replacing the opaque material with a partially transmissive or "halftone" film. A ternary attenuated PSM is an attenuated PSM that includes completely opaque features as well.

A reticle may become damaged over time in a number of different ways. In a first degradation example, the photolithographic exposure process may result in physical degradation of the opaque material of the reticle. For instance, a high power beam, such as a high powered deep ultra violet (UV) beam at 193 nm, that is used on the reticle may physically cause damage to the opaque material on the reticle. Damage may also be caused by other wavelengths, such as a 248 nm UV beam. In effect, the UV beam can physically cause the opaque patterns on the reticle to slump by blasting the corners off of opaque features and causing the features to flatten. This physical effect can adversely affect the critical dimensions (CD's) of the reticle.

FIG. 1A is a diagrammatic side view of a reticle portion 100 undergoing photolithographic exposure using a high power, deep ultra violet (UV) light 108. The reticle portion 100 includes opaque patterns 104a and 104b formed on transparent substrate 102. The opaque portions 104a and 104b substantially block the light 108, while the transparent portions pass the light 108 to the underlying wafer (not shown) to expose a photolithography film on such wafer that reacts to the incident light 108. The exposed regions of the film form a pattern on the wafer after further processing, such as an etching process to remove the exposed (or unexposed) film portions.

As shown, the opaque pattern structures 104a and 104b are designed and formed with critical dimension (CD) widths 106a and 106c, respectively. Similarly, the spacing between opaque features 104a and 104b has CD width 106b. A particular CD value may generally affect how such particular reticle feature is transferred to the wafer in the photolithography process and such CD is chosen to optimize this transfer process. Said in another way, if a certain reticle feature's CD value is within a specified CD range, such CD value will result in fabrication of a corresponding wafer feature that allows proper operation of the resulting integrated circuit as intended by the circuit designer. Features are typically formed with minimum dimensions that also result in operational circuits so as to conserve integrated chip area.

Figure 1B:
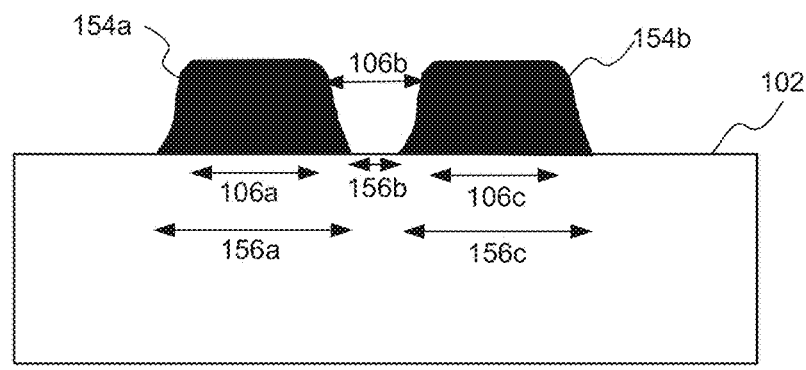
FIG. 1B is a diagrammatic side view of the reticle of FIG. 1A illustrating degradation of mask features due to repeated lithographic exposure.

The mask feature dimensions, e.g., 106a-c of FIG. 1A, may initially have CD values that meet predefined specifications. However, after repeated exposure to deep UV, for example, the mask features may degrade such that CD values are no longer within the predefined specifications. FIG. 1B is a diagrammatic side view of the reticle of FIG. 1A illustrating a physical type degradation of the mask features due to repeated lithographic exposure. This type of degradation is referred to as "chrome" degradation since this type of problem typically occurs in chrome type reticles.

During each exposure, deep UV light is applied to the reticle at relatively high power. This high power UV light tends to "push down" the opaque features, resulting in more rounded and flattened opaque features, such as 154a and 154b. The degraded features 154a and 154b show significantly altered dimensions 156a and 156c, as well as affecting the spacing width 156b. As shown, opaque features 154a and 154b have significantly larger widths 156a and 156c, as compared to original widths 106a and 106c, respectively, while the spacing between such opaque features has a much smaller width 156b, as compared with the original width 106b. As a result of this degradation, the feature CD values may have significantly changed so as to affect wafer yield. For instance, mask feature widths 156a and 156c may be significantly larger than the original line width CD, while the spacing width 156b may be significantly smaller than the original line spacing width CD.

Figure 1C:
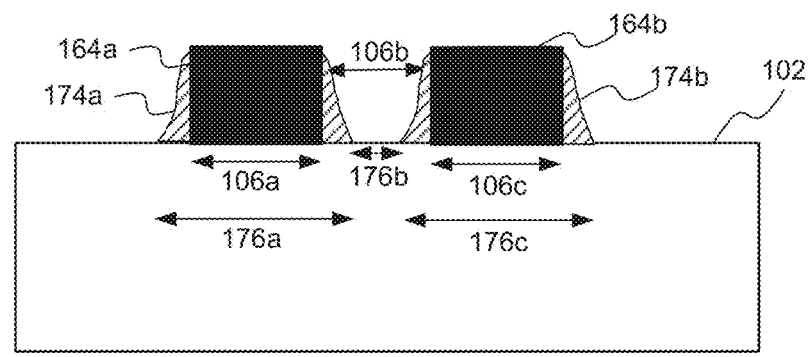
FIG. 1C illustrates degradation of a MoSi reticle portion that occurred during repeated photolithography exposure processes.

Another type of degradation occurs with MoSi reticles, in particular, but may also occur in other types of reticles. FIG. 1C illustrates degradation of a MoSi reticle portion that occurred during repeated photolithography exposure processes. During exposure, the light chemically reacts with the MoSi features 164a and 164b so as to cause an oxidation layer 174b and 174b to be formed on such MoSi features. That is, the light causes a photo-catalyzed chemical reaction so as to ionize oxygen from the MoSi material and cause oxidation of the surface of such MoSi features. This oxidation causes the opaque MoSi features 104a and 104b to become rounded by an oxidation build-up along the edges. This MoSi oxidation also causes the CD's to change. For instance, MoSi features 164a and 164b (along with extra oxidation material) results in a larger feature width CD of 176a and 176c, respectively, and a smaller spacing CD 176b.

Figure 2:
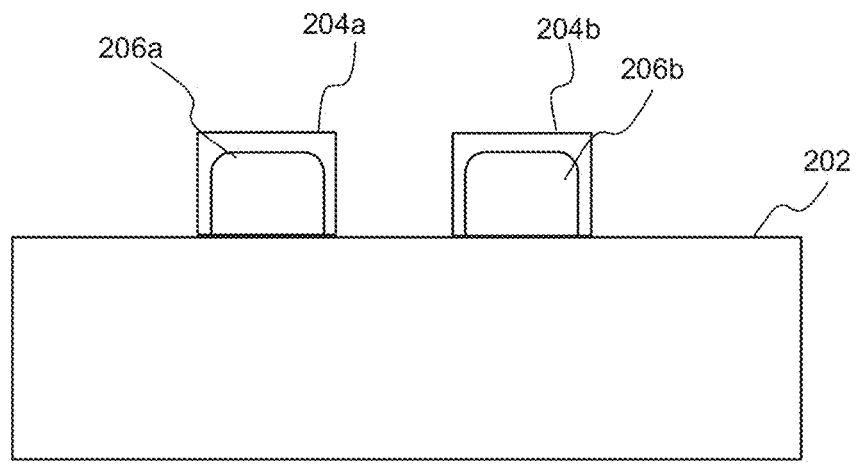
FIG. 2 illustrates erosion of reticle features due to a cleaning process.

In another degradation example, the opaque features may be made smaller by a cleaning process. Chemical contaminants from the air or other sources may be formed on the reticle surface to cause a "haze." This haze is typically cleaned off of the reticle. However, this cleaning process may cause erosion of the reticle features. FIG. 2 illustrates erosion of reticle features due to a cleaning process. Before cleaning, the reticle includes reticle features 204a and 204b of a particular size and shape on transparent substrate 202. During cleaning, the cleaning solution may cause these reticle features to erode to form eroded features 206a and 206b. Cleaning type degradation may also affect the wafer yield, especially as CD becomes smaller and smaller (e.g., 200 nm or lower).

Figure 3A:
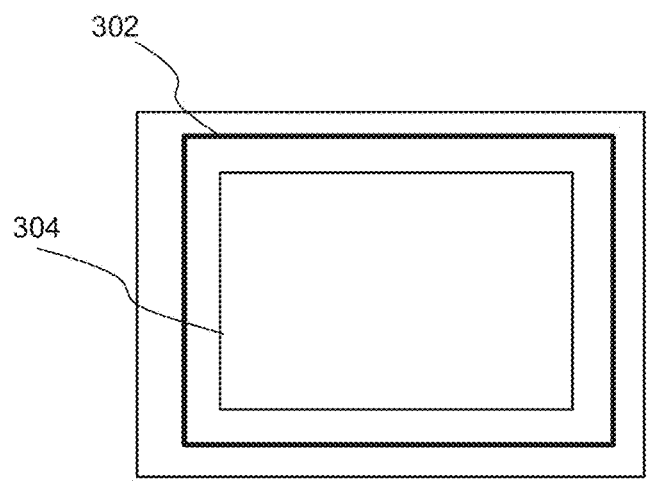
FIG. 3A is a top diagrammatic view of a reticle having an active region surrounded by a pellicle frame.
Figure 3B:
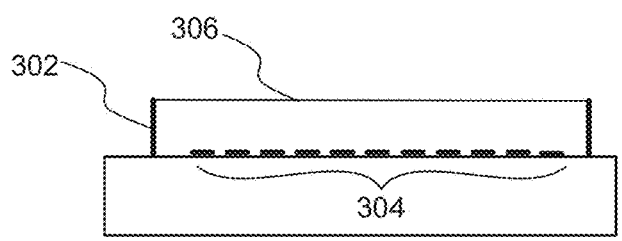
FIG. 3B shows a diagrammatic side view of the reticle and pellicle of FIG. 3A.

The pellicle of a reticle may also degrade over time. FIG. 3A is a top diagrammatic view of a reticle having an active region 302 surrounded by a pellicle frame 302. FIG. 3B shows a diagrammatic side view of the reticle and pellicle of FIG. 3A. The pellicle includes the pellicle frame 302 and a transparent film 306 supported by the pellicle frame 302. The pellicle is mounted on the reticle to protect the active region 304 from contamination. Since the lithography system has a relatively high numerical aperture, contaminants on the back of the reticle are not in focus and do not usually affect the exposure characteristics. However, the pellicle film may darken or otherwise change over time during exposure. Although the pellicle film 306 may be replaced with a new film, for example, after a cleaning process, it would be beneficial to monitor pellicle degradation in between cleanings. Pellicle degradation tends to be radial over time and may adversely affect wafer fabrication.

Certain embodiments provide techniques and systems for tracking the temporal degradation of a reticle, such as chrome, MoSi, pellicle, or cleaning type degradations using a temporal intensity variation map for specific areas defined substantially across the entire reticle. For example, average intensity variations for specific areas of the reticle are provided, for example, during a reticle inspection process. In a specific implementation, the reticle's active area is defined as a plurality of patch areas. An optical tool is used to inspect the reticle and obtain an average intensity value for each patch area before and after such reticle undergoes multiple exposure processes. An intensity map is then generated based on temporal variations of average intensity values for the same patch areas.

Embodiments of a temporal intensity variation map can take any suitable form. For example, the intensity map can be represented textually as a list of average intensity variation values for each area of the reticle. For instance, each average intensity variation value may be listed alongside corresponding reticle area coordinates. It can also be represented by a metric such as the standard deviation or variance of the grid point difference values. Alternatively or additionally, a temporal intensity variation map may be represented visually so that different intensity variation values or ranges are shown as different visual ways, such as differently colored reticle areas, different bar graph heights, different graph values, or 3-dimensional representations, etc. An intensity map can be represented with different grid point sampling sizes or by fits to different functional forms such as a polynomial fit or a Fourier transform.

Figure 4:
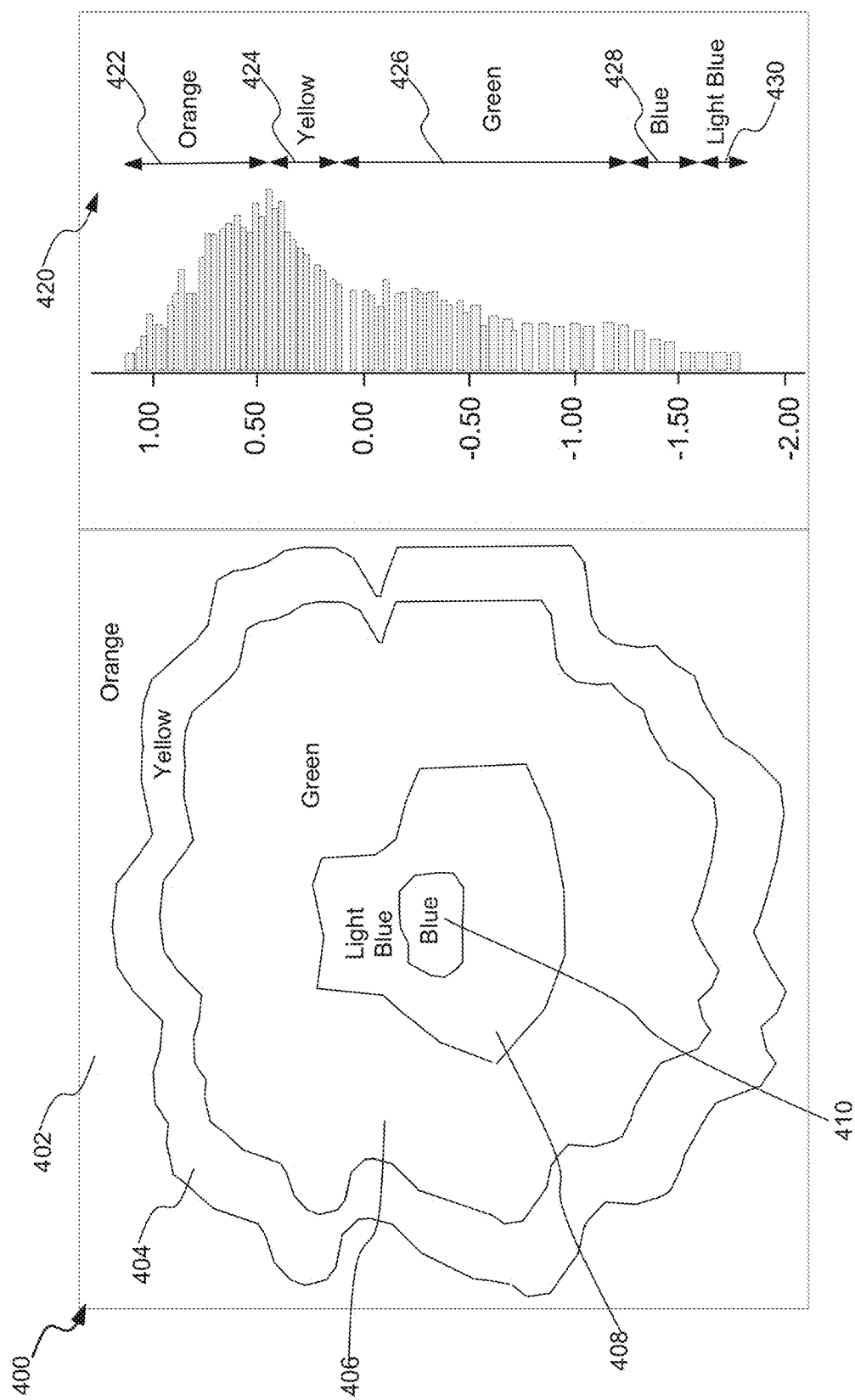
FIG. 4 is a diagrammatic representation of a temporal intensity variation map that is generated based on the difference in average intensities over time at particular areas across the reticle in accordance with one embodiment of the present invention.

FIG. 4 is a diagrammatic representation of a temporal intensity variation map 400 that is generated based on the difference in average intensities over time at particular areas across the reticle in accordance with one embodiment of the present invention. In a specific example, an analysis process may be used to generate a difference intensity map from two inspections that were performed before and after multiple exposure runs. A difference intensity map 400 may be displayed on any suitable graphical user interface (GUI) provided on a display of, for example, a computer, or any other suitable type of human interface, such as a textual and/or auditory interface.

The illustrated intensity map 400 corresponds to the entire active area of the reticle. Although not shown in color, the intensity map 400 may include different color regions that correspond to different regions of the reticle that have different intensity changes over time. As shown, the intensity map 400 includes a blue center region 410, a light blue inner ring region 408, a green outer ring region 406, and yellow and orange outer-most regions 404 and 402. In this example, the green region corresponds to a zero intensity difference for this particular region of the reticle, while blue, light-blue, yellow, and orange regions correspond to different intensity differences for these particular reticle regions over time.

The user interface may include other mechanisms for representing intensity variations for the reticle. As shown, the user interface may also include a bar graph 420 that is generated from two inspections that were performed before and after multiple exposure runs. The bar graph includes counts of intensity variation values having ranges 422, 424, 426, 428, and 430 that are normalized to a zero mean. Each range may also be displayed with a particular color. For instance, range 422 is orange; range 424 is yellow; range 426 is green, range 428 is blue; and range 430 is light blue. Of course, different ranges may be assigned to different colors or values and depends on the particular application.

Certain intensity map embodiments illustrate intensity changes in both a spatial and temporal dimension for the different regions of the reticle. For instance, a temporal intensity variation map corresponds to how much light on average is transmitted through or is reflected from specific larger areas of the reticle. These intensity maps illustrate average temporal and spatial variation without having to resolve defects on a fine scale resolution. A temporal intensity variation map may be generated and applied to non-repeating reticle features, as well as repeating reticle features.

Figure 5:
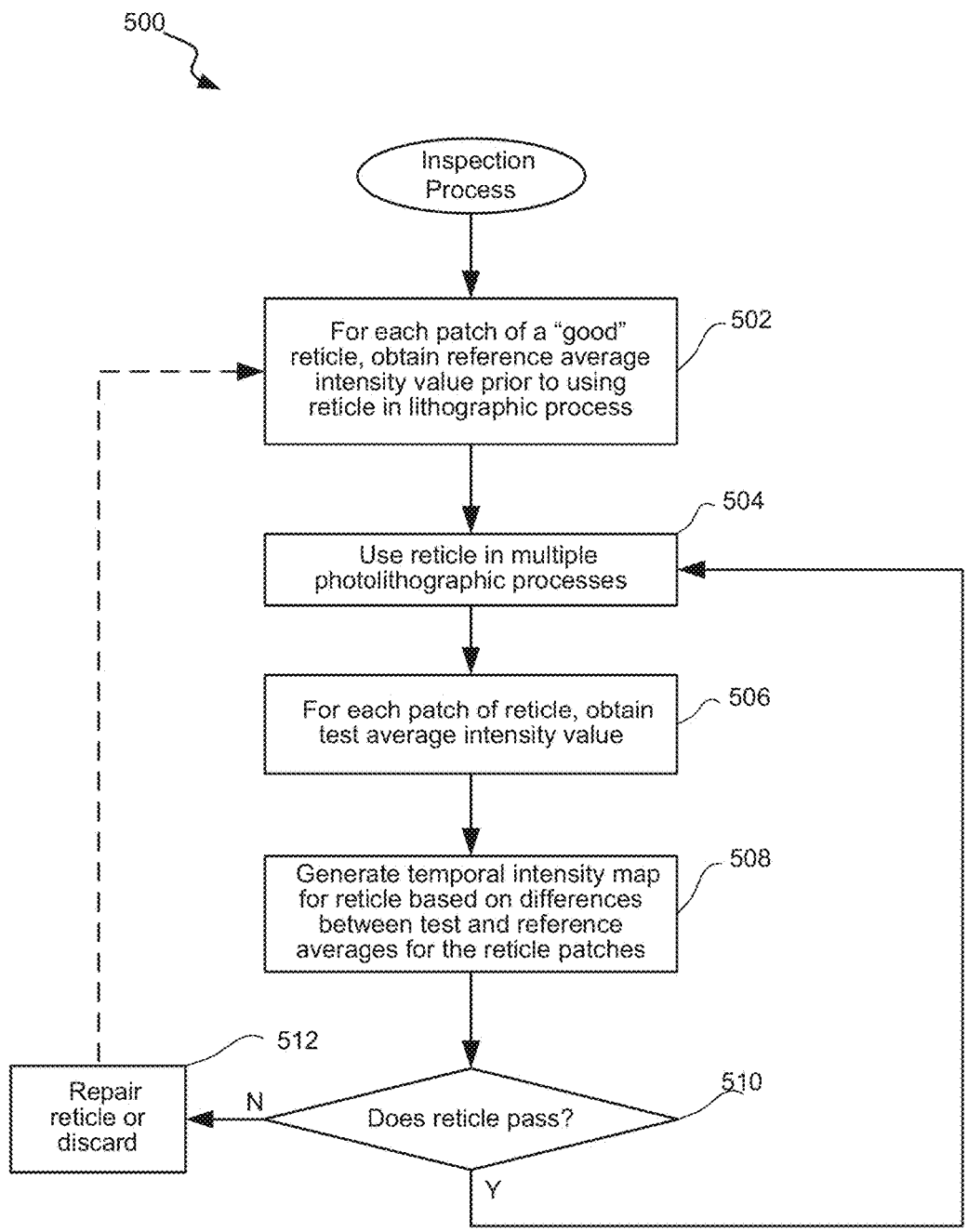
FIG. 5 is a flow chart illustrating a reticle inspection process in accordance with one embodiment of the present invention.

FIG. 5 is a flow chart illustrating a reticle inspection process 500 in accordance with one embodiment of the present invention. Initially, a reference average intensity value (for multiple intensity values in the patch or set of patches) may be obtained for each patch (or set of patches) of the "good" reticle prior to using the reticle in a photolithography process in operation 502. The reference inspection procedure is generally performed with respect to a known good reticle. Accordingly, a new reticle that is verified as free of degradation and defects, for example, is used to obtain reference average intensity values during a reference inspection process. Alternatively, reference average intensities may be obtained for each patch after a reticle has undergone any type of process that may affect reticle degradation or CD. For instance, reference average intensities may be obtained after photolithography processes have been repeatedly implemented with the reticle and after the reticle is cleaned and verified to have minimal or no degradation or defects.

A reticle may be verified or defined as having substantially no degradation or defects by any suitable manner. For example, a buyer of a newly manufactured reticle may assume that the reticle has been verified by the manufacturer as free of defects and degradation. Alternatively, the reticle may be inspected with an optical or scanning electron microscope to determine whether there are any CD uniformity defects on the reticle or the reticle has degraded, for example, by performing a die-to-database inspection. A reticle may be similarly inspected after cleaning to remove haze, as well as other types of degradation and defects.

The reticle is generally divided into a plurality of patch portions from which multiple intensity values from multiple points are obtained. The patch portions of the reticle can be scanned to obtain this intensity data. The patch portions may be any size and shape, depending on the particular system and application requirements. In general, multiple intensity values for each patch portion may be obtained by scanning the reticle in any suitable manner. By way of example, multiple intensity values for each patch portion may be obtained by raster scanning the reticle. Alternatively, the images may be obtained by scanning the reticle with any suitable pattern, such as a circular or spiral pattern. Of course, the sensors may have to be arranged differently (e.g., in a circular pattern) and/or the reticle may be moved differently (e.g., rotated) during scanning in order to scan a circular or spiral shape from the reticle.

In the example illustrated below, as the reticle moves past the sensors, light is detected from a rectangular region (herein referred to as a "swath") of the reticle and such detected light is converted into multiple intensity values at multiple points in each patch. In this embodiment, the sensors of the scanner are arranged in a rectangular pattern to receive light that is reflected and/or transmitted from the reticle and generate therefrom a set of intensity data that corresponds to a swath of patches of the reticle. In a specific example, each swath can be about 1 million pixels wide and about 1000 to 2000 pixels high, while each patch can be about 2000 pixels wide and 1000 pixels high.

Figure 6A:
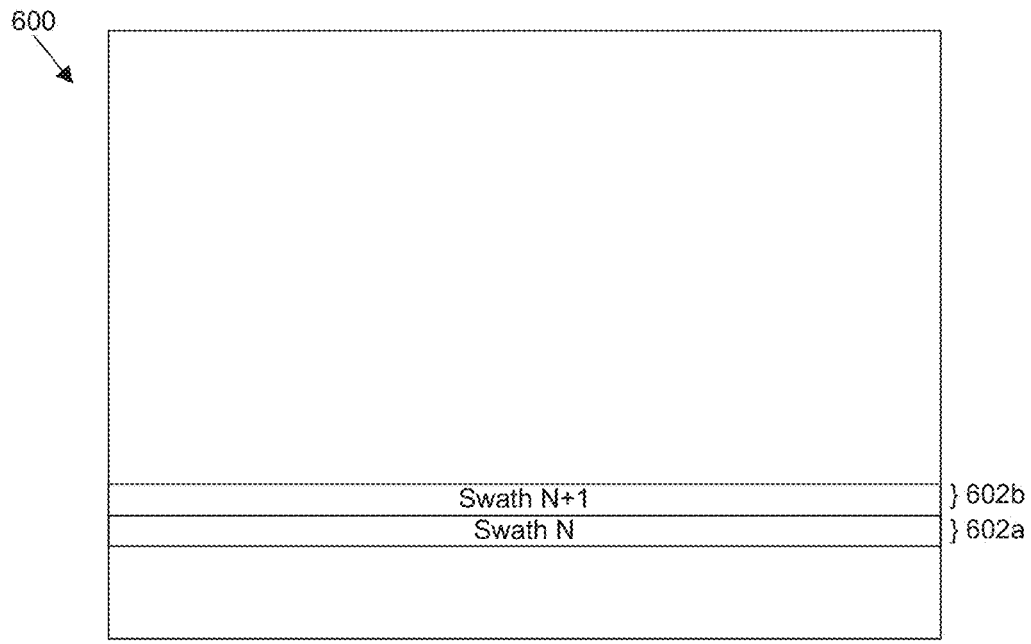
FIG. 6A is a diagrammatic representation of two sets of intensity data corresponding to two "swaths" of a reticle in accordance with embodiment of the present invention.
Figure 6B:
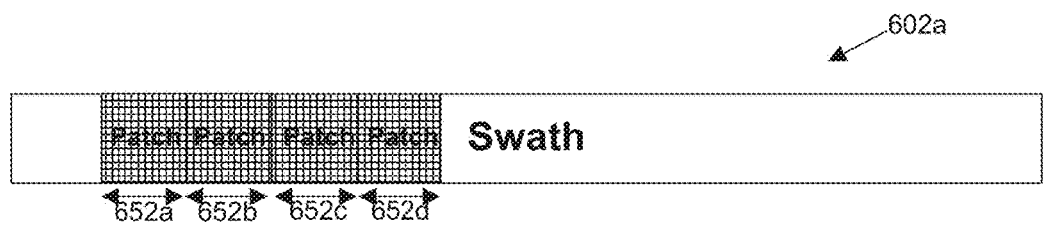
FIG. 6B is a diagrammatic illustration of an intensity data set that corresponds to a swath that is divided into patches in accordance with a specific implementation.

FIG. 6A is a diagrammatic representation of two sets of intensity data corresponding to two "swaths" 602a and 602b of a reticle 600 in accordance with embodiment of the present invention. Each set of intensity data may correspond to a "swath" of the reticle 600. Each set of intensity data may be obtained by sequentially scanning swaths from the reticle in a serpentine or raster pattern. For example, the first swath 602 of the reticle 600 is scanned by an optical beam of an optical inspection system from left to right to obtain a first set of intensity data. The second swath 604 is then scanned from right to left to obtain a second set of intensity data. FIG. 6B is a diagrammatic illustration of the intensity data set 602a, which corresponds to swath that is divided into patches. As shown, the intensity data 602a further includes the intensity data for a plurality of patches, such as such intensity data sets 652a, 652b, 652c, and 652d corresponding to patches of a swath of a reticle.

Figure 6C:
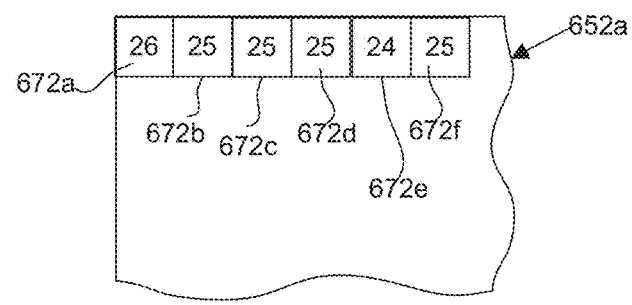
FIG. 6C illustrates multiple intensity values corresponding to multiple pixels or points of a particular patch of a particular swath of a reticle.

During or after intensity data is collected for multiple points in each patch of each swath, an average intensity value may also be determined for each patch or set of one or more patches. FIG. 6C illustrates multiple intensity values (e.g., 672a, 672b, 672c, 672d, 672e, and 672f) corresponding to multiple pixels or points of a particular patch 652a of a particular swath of a reticle. For example, intensity data set 652a corresponding to a patch of the reticle may include intensity values 26, 25, 25, 25, 24, 25, etc. All of the intensity values for each patch may be averaged together to determine an average intensity value (e.g., 25) for such patch.

Referring back to the inspection process of FIG. 5, the "good" reticle may then be used in multiple photolithography processes in operation 504 after average intensity values are obtained for each patch of the "good" reticle. A test average intensity value may then be obtained for each patch (or set of patches) of the reticle in operation 506. The test average for each patch may be obtained similarly as the technique used to obtain the reference average for each patch.

Intensity values for each patch may be obtained using an optical inspection tool that is set up in any suitable manner. The optical tool is generally set up with a set of operating parameters or a "recipe" that is substantially the same for the different inspection runs for obtaining intensity values. Recipe settings may include one or more of the following settings: a setting for scanning the reticle in a particular pattern, pixel size, a setting for grouping adjacent signals from single signals, a focus setting, an illumination or detection aperture setting, an incident beam angle and wavelength setting, a detector setting, a setting for the amount of reflected or transmitted light, aerial modeling parameters, etc.

A temporal intensity map for the reticle may then be generated based on the differences between test and reference averages for the reticle patches in operation 508. For example, the test and reference average for the same patch or each set of patches are subtracted from each other to determine a difference average for the same patch or set of patches. A global offset may also be determined and subtracted from each difference value prior to generating the temporal intensity map. For instance, the mean of the entire reticle (e.g., average of all patch averages or average of all intensity values) is determined and subtracted from each difference value (or each pixel intensity value difference) so as to eliminate global intensity changes from the temporal intensity map.

It may be beneficial to remove any global changes prior to generating a temporal intensity map. For instance, the light calibration may vary between the reference and test inspection and cause an overall offset in the detected light that is not related to reticle's level of degradation. Additionally, degradation does not tend to be uniform. Additionally, the photolithography tool may be programmed to compensate for uniform changes so that uniform changes may not adversely affect the exposure process, as opposed to non-uniform changes for which it is difficult to compensate during the photolithography process. In view of the forgoing, a global offset may often be reasonably disregarded and removed from the intensity map results so that the map only provides non-uniform changes.

However, a uniform intensity offset may be important in other applications. Accordingly, the temporal intensity map may be formed without removing any global offset. For instance, a global intensity offset may be used to determine a global CD variation. That is, a global CD variation may be associated with a temporal intensity map's global intensity offset. Both the transmitted and reflected light signal may be analyzed to compensate for noise while determining a global CD change. The parts of the R and T maps that "agree" can be used for determining a CD offset, while the parts of those that "disagree" imply noise of some type (i.e., birefringence, reflectivity changes) and are not used for determining a CD offset. It is also preferable that the inspection light levels are properly calibrated and compensated.

One way to determine a global offset is to compute the full mask mean for the test and reference inspections and subtract the results. In most cases, this mean result is subtracted from the temporal intensity map results. However, for relatively noise-free results, the global offset can be very meaningful, for example, even if there was no apparent spatial distribution change. This global offset can represent the global CD change.

After a temporal intensity map is provided, it may then be determined whether the reticle passes inspection based on such map in operation 510. For instance, it may be determined whether any variation in average intensity values over time for a same reticle area is above a predefined threshold. If an average temporal intensity variation is above the predefined threshold, the corresponding reticle portion may then be more carefully reviewed to determine whether the reticle is defective and can no longer be used. For instance, a SEM may be used to review the defective area to determine whether critical dimensions (CD's) are out of specification.

In alternative implementations, specific intensity changes in the temporal intensity map can be associated with specific CD values, which can then be determined to be in or out of specification. Particular intensity changes may be associated with specific CD values through calibration reticles having multiple known CD values that can be measured to determine intensity differences between different CD changes. Although these CD and intensity change correlations are obtained from different areas of the calibration reticle, these associations may be applied to each temporal intensity difference for each same reticle area to determine temporal CD variation for such same reticle area.

An out-of-specification CD would result in the reticle not passing the inspection. If the reticle fails inspection, the reticle may be discarded or repaired if possible in operation 512. For instance, certain defects can be cleaned from the reticle. After repair, a new reference inspection may be performed on the cleaned reticle and the procedure repeated.

Figure 7:
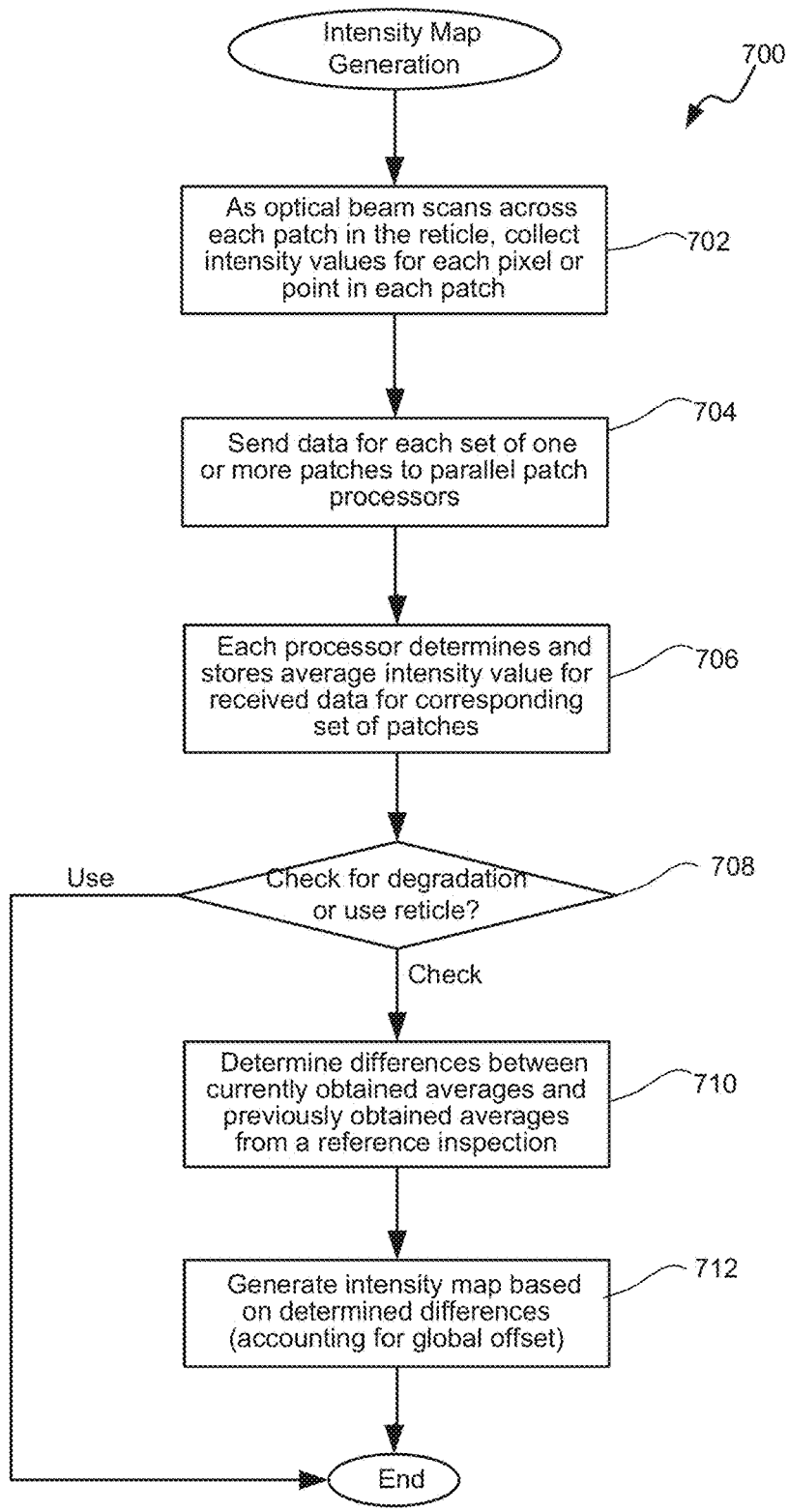
FIG. 7 is a flow chart illustrating a procedure for generating a temporal intensity map according to a specific implementation of the present invention.

FIG. 7 is a flow chart illustrating a procedure 700 for generating a temporal intensity map according to a specific implementation of the present invention. Initially, an optical beam may scan across the reticle and intensity values may be collected for each pixel or point in each patch as such beam scans across each patch in operation 702. Said in another way, the inspection tool may be operable to detect and collect reflected or transmitted light or both reflected and transmitted light as an incident optical beam scans across each patch of a reticle. As noted above, the incident optical beam may scan across reticle swaths that each comprises a plurality of patches. Light is collected in response to this incident beam from a plurality of points or subareas of each patch.

The inspection tool may be generally operable to convert such detected light into detected signals corresponding to intensity values. The detected signals may take the form of an electromagnetic waveform having amplitude values that correspond to different intensity values at different locations of the reticle. The detected signals may also take the form of a simple list of intensity values and associated reticle point coordinates. The detected signals may also take the form of an image having different intensity values corresponding to different positions or scan points on the reticle. A reticle image may be generated after all the positions of the reticle are scanned and converted into detected signals, or portion of a reticle image may be generated as each reticle portion is scanned with the final reticle image being complete after the entire reticle is scanned.

The detected signals may also take the form of aerial images. That is, an aerial imaging technique may be used to simulate the optical effects of the photolithography system so as to produce an aerial image of the photoresist pattern that is exposed on the wafer. In general, the optics of the photolithography tool are emulated so as to produce an aerial image based on the detected signals from the reticle. The aerial image corresponds to the pattern produced from the light passed through the photolithography optics and reticle onto the photoresist layer of a wafer. Additionally, the photoresist exposure process for the particular type of photoresist material may also be emulated.

The incident light or detected light may be passed through any suitable spatial aperture to produce any incident or detected light profile at any suitable incident angles. By way of examples, programmable illumination or detection apertures may be utilized to produce a particular beam profile, such as dipole, quadrapole, quasar, annulus, etc. In a specific example, Source Mask Optimization (SMO) or any pixelated illumination technique may be implemented.

The data for the detected signals for each set of one or more patches may be sent to parallel patch processors in operation 704. For instance, the intensity values for a first patch may be sent to a first processor, and the intensity values for a second patch may be sent to a second processor. Alternatively, the data for a predefined number of patches may be sent to individual patch processors.

Each processor may determine and store average patch intensity values for each set of one or more patches in operation 706. For instance, each processor may determine an average of one patch or an average for each set of multiple patches. For example, an average may be determined for each set of 1, 2, 50, or 200 patches. The number of patches for which an average is determined, of course, affects the sampling granularity. That is, a higher number of patches for each average calculation is associated with a lower sampling number. However, noise is reduced as more patches are used to determine each average.

Certain embodiments of the present invention allow higher number of points to be sampled, as compared to other inspection techniques, for example, as performed with a SEM. Since an SEM inspection is very slow, sparse sampling (e.g., typically not more than 2000 points) is often used. In one example implementation of the present invention, each patch (1 k×2 k) contains about 2 million pixels that are scanned to obtain intensity values for all 2 million points of each pixel. If an average is obtained for each patch, 2 million points are sampled. In another example, averaging the points in 2 patches results in 1 million points being sampled for each 2-patch grid. If 50 patches are averaged, 40,000 points are sampled for each 50-patch grid. Averaging 200 patches results in 10,000 points being sampled, which is still much higher than the maximum number of points one may wish to sample in an SEM inspection.

The intensity values corresponding to the reflected light may also be combined with the intensity values for the transmitted light before or after determining the average intensity value for each patch. For instance, an average of the reflected and transmitted intensity values may be determined for each point or pixel. Alternatively, the averages may be calculated separately for the reflected and transmitted intensity values of a patch. The separately calculated reflected average and transmitted average for each patch may also be combined or averaged together. In sum, the temporal intensity variation maps may be generated based on reflected light, transmitted light, or both as detected during reticle inspections. In one example implementation, the reflected (R) and transmitted (T) values may be combined by (T−R)/2. The reflected signal typically is the opposite sign from the transmitted signal. Hence, subtracting the two maps adds the signals together. Since the noise sources are different for T and R, the noise can tend to be averaged out of the combined signal. Other weightings to R and/or T values may be used to generate a final combination map with associated benefits. In some cases, R and T signals for particular regions may have a same sign, instead of an opposite sign, which may indicate that the results are inconsistent in the associated regions and may not be trustworthy. Thus, the combination of R and T could be down-weighted in such regions or removed from the computation if insufficiently trustworthy.

Referring back to the illustrated example of FIG. 7, it may then be determined whether a degradation check is to commence or the reticle is to be used in a photolithography process in operation 708. For instance, if the reticle is new and has not been previously inspected, the reticle is simply used. After multiple uses and intensity data is collected again for the same reticle, it may be determined that it is time to check the reticle for degradation in operation 708.

The differences between the currently obtained intensity averages and a set of previously obtained intensity averages may then be determined in operation 710. That is, each average intensity value that was determined for one or more patches at the current time is subtracted from each average intensity value for the same one or more patches that was determined at an earlier time (or visa versa). For instance, the average of the intensity values of a particular patch at a first time, $t_0$, is subtracted from the average of the intensity values of the same particular patch (or set of patches) at a second time, $t_1$. This subtraction process in repeated for the averages obtained at time $t_0$ and $t_1$ for each patch (or set of patches) of a particular reticle.

An intensity map for the reticle may then be generated based on the determined average differences in operation 712. The intensity map may include one or more global offsets or be generated to exclude any global offsets. That is, if the average intensity of substantially all of the patches has an increased or decreased on average by a certain global intensity change from time $t_0$ to $t_1$, this change can be subtracted from each patch average for time $t_1$ that is determined prior to generating the intensity map for times $t_0$ and $t_1$.

An intensity map can be generated to show changes in average intensity values across the reticle over time. For instance, if a patch of the reticle has not changed from time $t_0$ to $t_1$, the intensity map will show no change for this patch for this timeframe. Since the two sets of intensity data were obtained at two different times using the same inspection recipe, it is easy to align data from identical patches on the reticle. For instance, each inspection process has the same scan pattern and collects data from specific positions of the reticle that correspond to specific patches at locations relative to a same reticle origin position. The data for each patch includes position data and corresponding intensity values for the particular patch relative to an origin position. Thus, when a same inspection process is used, the data for a particular patch will be associated with the same position data as the previous inspection relative to the same reticle origin position. The difference intensity map can be based on finding differences between average intensity data from two different times that is also associated with the same set of locations (e.g., same reticle patch or set of patches).

An intensity map may be generated for the active region of the reticle while the pellicle is attached or after the pellicle is removed (e.g., to be replaced). The active region is the reticle pattern portion that is used to generate corresponding patterns on the wafer during the lithography process. That is the reticle active region is used to generate a plurality of die regions of the wafer. If the pellicle is present, the intensity difference map may show degradation of the reticle active region, pellicle, or both.

The intensity difference map will tend to show only non-uniform degradation if any global change offsets are removed. For instance, the intensity difference map may show a radial degradation pattern across the reticle or pellicle. Intensity differences may vary based on different density levels of the active region. For instance, a same degradation may show more clearly in the intensity map in regions corresponding to higher density active regions of the reticle.

The temporal intensity map may be generated so as to compensate for pattern density effects. Since the intensity changes are dependent on the number of edge pixels, the intensity difference value for each patch can be scaled based on the average number of edge pixels. For instance, each particular patch average can be scaled (reduced or increased) by the average number of edge pixels for all of the patches in the reticle divided by the particular patch's number of edge pixels. If a patch has no edges (e.g., empty), this scaling would not be performed for such patch so as to not divide by zero.

Certain embodiments of the present invention may be applied to non-repeating logic patterns, as well as repeating patterns. Since intensity maps are generated for the same patch (or set of patches) at different times, rather than for repeating cell portions at the same time, differences can be found for patches that do not form part of a repeating pattern. Additionally, since the intensity difference maps are generated for the same patches of the entire reticle over time, this intensity map will clearly show a change in the reticle's spatial profile, such as a radial change across the reticle over time due to chrome degradation.

Figure 8:
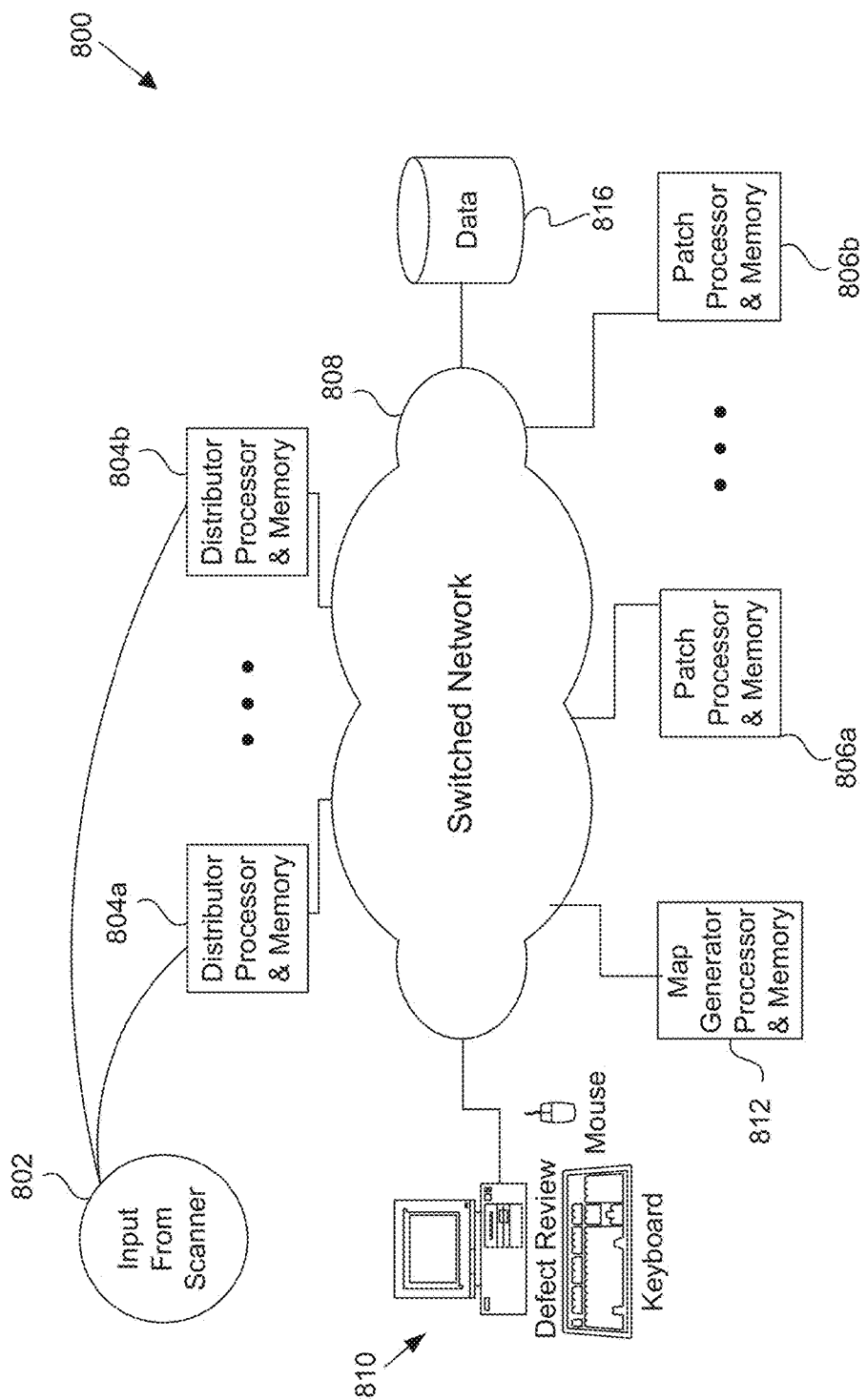
FIG. 8 is a diagrammatic representation of an example inspection system in which techniques of the present invention may be implemented

Techniques of the present invention may be implemented in any suitable combination of hardware and/or software. FIG. 8 is a diagrammatic representation of an example inspection system 800 in which techniques of the present invention may be implemented The inspection system 800 may receive input 802 from an inspection tool or scanner (not shown). The inspection system may also include a data distribution system (e.g., 804a and 804b) for distributing the received input 802, an intensity signal (or patch) processing system (e.g., patch processors and memory 806a and 806b) for processing specific portions/patches of received input 802, a map generator system (e.g., Map Generator Processor and Memory 812) for generating a temporal intensity map, a network (e.g., switched network 808) for allowing communication between the inspection system components, an optional mass storage device 816, and one or more inspection control and/or review stations (e.g., 810) for reviewing the temporal intensity maps. Each processor of the inspection system 800 typically may include one or more microprocessor integrated circuits and may also contain interface and/or memory integrated circuits and may additionally be coupled to one or more shared and/or global memory devices.

The scanner or data acquisition system (not shown) for generating input data 802 may take the form of any suitable instrument (e.g., as described further herein) for obtaining intensity signals or images of a reticle. For example, the scanner may construct an optical image or generate intensity values of a portion of the reticle based on a portion of detected light that is reflected, transmitted, or otherwise directed to one or more light sensors. The scanner may then output the intensity values or image may be output from the scanner.

Intensity or image data 802 can be received by data distribution system via network 808. The data distribution system may be associated with one or more memory devices, such as RAM buffers, for holding at least a portion of the received data 802. Preferably, the total memory is large enough to hold an entire swatch of data. For example, one gigabyte of memory works well for a swatch that is 1 million by 1000 pixels or points.

The data distribution system (e.g., 804a and 804b) may also control distribution of portions of the received input data 802 to the processors (e.g. 806a and 806b). For example, data distribution system may route data for a first patch to a first patch processor 806a, and may route data for a second patch to patch processor 806b. Multiple sets of data for multiple patches may also be routed to each patch processor.

The patch processors may receive intensity values or an image that corresponds to at least a portion or patch of the reticle. The patch processors may each also be coupled to or integrated with one or more memory devices (not shown), such as DRAM devices that provide local memory functions, such as holding the received data portion. Preferably, the memory is large enough to hold data that corresponds to a patch of the reticle. For example, eight megabytes of memory works well for intensity values or an image corresponding to a patch that is 512 by 1024 pixels. Alternatively, the patch processors may share memory.

Each set of input data 802 may correspond to a swath of the reticle. One or more sets of data may be stored in memory of the data distribution system. This memory may be controlled by one or more processors within the data distribution system, and the memory may be divided into a plurality of partitions. For example, the data distribution system may receive data corresponding to a portion of a swath into a first memory partition (not shown), and the data distribution system may receive another data corresponding to another swath into a second memory partition (not shown). Preferably, each of the memory partitions of the data distribution system only holds the portions of the data that are to be routed to a processor associated with such memory partition. For example, the first memory partition of the data distribution system may hold and route first data to patch processor 806a, and the second memory partition may hold and route second data to patch processor 806b.

The data distribution system may define and distribute each set of data of the data based on any suitable parameters of the data. For example, the data may be defined and distributed based on the corresponding position of the patch on the reticle. In one embodiment, each swath is associated with a range of column positions that correspond to horizontal positions of pixels within the swath. For example, columns 0 through 256 of the swath may correspond to a first patch, and the pixels within these columns will comprise the first image or set of intensity values, which is routed to one or more patch processors. Likewise, columns 257 through 512 of the swath may correspond to a second patch, and the pixels in these columns will comprise the second image or set of intensity values, which is routed to different patch processor(s).

Figure 9A:
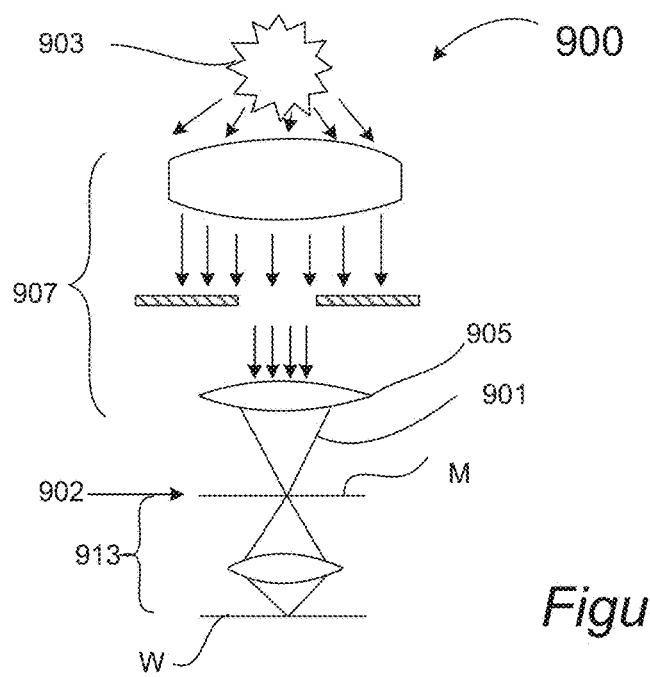
FIG. 9A is a simplified schematic representation of a lithographic system for transferring a mask pattern from a photomask onto a wafer in accordance with certain embodiments.

FIG. 9A is a simplified schematic representation of a typical lithographic system 900 that can be used to transfer a mask pattern from a photomask M onto a wafer W in accordance with certain embodiments. Examples of such systems include scanners and steppers, more specifically PAS 5500 system available from ASML in Veldhoven, Netherlands. In general, an illumination source 903 directs a light beam through an illumination optics 901 (e.g., lens 905) onto a photomask M located in a mask plane 902. The illumination lens 905 has a numeric aperture 901 at that plane 902. The value of the numerical aperture 901 impacts which defects on the photomask are lithographic significant defects and which ones are not. A portion of the beam that passes through the photomask M forms a patterned optical signal that is directed through imaging optics 913 and onto a wafer W to initiate the pattern transfer.

Figure 9B:
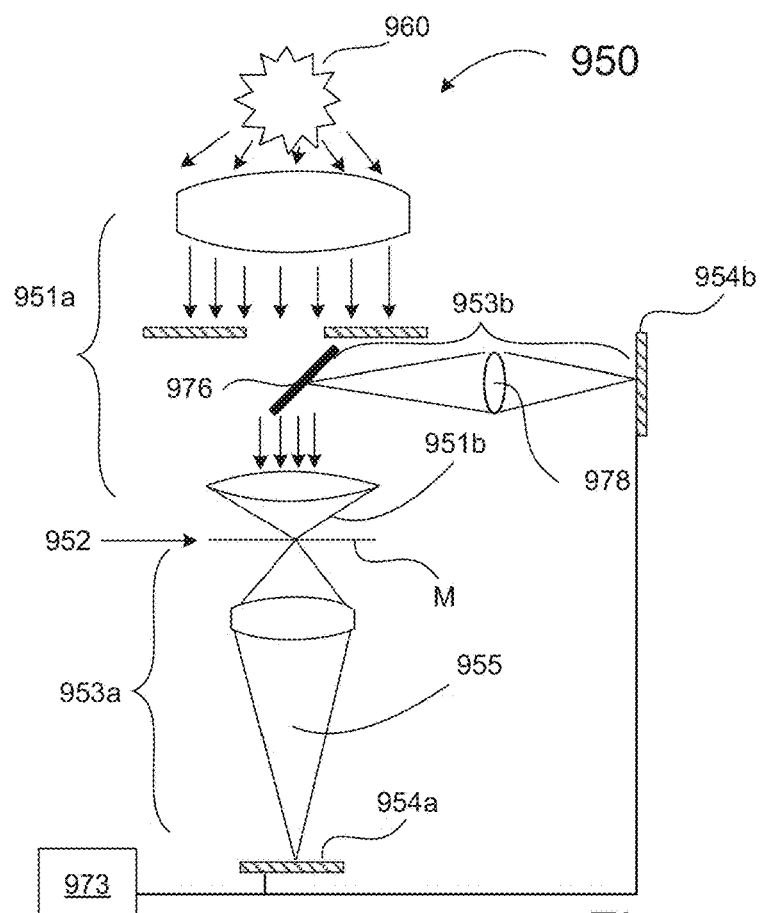
FIG. 9B provides a schematic representation of a photomask inspection apparatus in accordance with certain embodiments.

FIG. 9B provides a schematic representation of an example inspection system 950 that has illumination optics 951a includes an imaging lens with a relative large numerical aperture 951b at a reticle plane 952 in accordance with certain embodiments. The depicted inspection system 950 includes detection optics 953a and 953b, including microscopic magnification optics designed to provide, for example, 60-200× magnification or more for enhanced inspection. For example, the numerical aperture 951b at the reticle plane 952 of the inspection system may be considerable greater than the numerical aperture 901 at the reticle plane 902 of the lithography system 900, which would result in differences between test inspection images and actual printed images.

The inspection techniques described herein may be implemented on various specially configured inspection systems, such as the one schematically illustrated in FIG. 9B. The illustrated system 950 includes an illumination source 960 producing a light beam that is directed through illumination optics 951a onto a photomask M in the reticle plane 952. Examples of light sources include lasers or filtered lamps. In one example, the source is a 193 nm laser. As explained above, the inspection system 950 may have a numerical aperture 951b at the reticle plane 952 that may be greater than a reticle plane numerical aperture (e.g., element 901 in FIG. 9A) of the corresponding lithography system. The photomask M to be inspected is placed on a mask stage at the reticle plane 952 and exposed to the source.

The patterned image from the mask M is directed through a collection of optical elements 953a, which project the patterned image onto a sensor 954a. In a reflecting system, optical elements (e.g., beam splitter 976 and detection lens 978) direct and capture the reflected light onto sensor 954b. Suitable sensors include charged coupled devices (CCD), CCD arrays, time delay integration (TDI) sensors, TDI sensor arrays, photomultiplier tubes (PMT), and other sensors.

The illumination optics column may be moved respect to the mask stage and/or the stage moved relative to a detector or camera by any suitable mechanism so as to scan patches of the reticle. For example, a motor mechanism may be utilized to move the stage. The motor mechanism may be formed from a screw drive and stepper motor, linear drive with feedback position, or band actuator and stepper motor, by way of examples.

The signals captured by each sensor (e.g., 954a and/or 954b) can be processed by a computer system 973 or, more generally, by one or more signal processing devices, which may each include an analog-to-digital converter configured to convert analog signals from each sensor into digital signals for processing. The computer system 973 typically has one or more processors coupled to input/output ports, and one or more memories via appropriate buses or other communication mechanisms.

The computer system 973 may also include one or more input devices (e.g., a keyboard, mouse, joystick) for providing user input, such as changing, such as changing focus and other inspection recipe parameters. The computer system 973 may also be connected to the stage for controlling, for example, a sample position (e.g., focusing and scanning) and connected to other inspection system components for controlling other inspection parameters and configurations of such inspection system components.

The computer system 973 may be configured (e.g., with programming instructions) to provide a user interface (e.g., a computer screen) for displaying resultant intensity values, images, and other inspection results. The computer system 973 may be configured to analyze intensity, phase, and/or other characteristics of reflected and/or transmitted sensed light beam. The computer system 973 may be configured (e.g., with programming instructions) to provide a user interface (e.g., on a computer screen) for displaying resultant intensity values, images, and other inspection characteristics. In certain embodiments, the computer system 973 is configured to carry out inspection techniques detailed above Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, a system for inspecting a photomask includes at least one memory and at least one processor that are configured to perform techniques described herein. One example of an inspection system includes a specially configured TeraScan™ DUV inspection system available from KLA-Tencor of Milpitas, Calif.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of inspecting a photolithographic reticle, the method comprising:

during a first time period and prior to using a reticle in any photolithography process for fabricating semiconductor wafers, using an optical reticle inspection tool during a first inspection to direct an incident beam towards each of a plurality of sets of one or more patch areas of the reticle and then, in response to the incident beam, measure a plurality of reference intensity measurements from a plurality of sub-areas of each patch area, wherein the patch area sets substantially comprise the entire active areas of the reticle;

for measurements obtained during the first time period, determining a reference average for each patch area set by averaging the plurality of reference intensity measurements from the plurality of sub-areas of the patch area set;

after using the reticle in a plurality of photolithography processes for fabricating semiconductor wafers and during a second time period that differs from the first time period, using the optical reticle inspection tool during a second inspection to direct an incident beam towards each of the patch area sets and then in response to the incident beam measure a plurality of test intensity measurements from a plurality of sub-areas of each patch area set;

for measurements obtained during the second time period, determining a test average for each patch area set by averaging the plurality of test intensity measurements from the plurality of sub-areas of the patch area set, wherein a same setup recipe for the optical reticle inspection tool is used for both the first and second inspections so that the test average for each patch area set has a same location and aligns with the reference average for such same patch area set of the reticle; and for each of the patch area sets, determining an intensity difference between each aligned reference average, which was determined for each patch area set during the first time period, and test average, which was determined for each patch area set during the second time period, and representing and displaying on a display such intensity difference visually in a difference intensity map for qualifying the reticle for further use so that different values or ranges for the intensity differences are shown in different visual ways and such difference intensity map shows relative positions of the intensity differences for the patch area sets comprising the entire active areas of the reticle to display changes in intensity across the reticle during the differing first and second time periods.

2. The method of claim 1, further comprising determining whether to stop use of the reticle in a photolithography process for fabricating semiconductor wafers based on a defect review of the intensity differences that are determined to be above a predefined threshold.

3. The method of claim 1, wherein the first and second inspections are performed while a pellicle is mounted on the reticle and the difference intensity map indicates whether a pellicle of the reticle has degraded over time more than a predefined level.

4. The method of claim 1, wherein the difference intensity map indicates that the reticle has degraded in a spatially radial pattern over time more than a predefined level.

5. The method of claim 1, wherein each of the sets of one or more patch areas consists of a single patch area.

6. The method of claim 1, further comprising repairing or discarding the reticle if the difference intensity map is indicative of such action; otherwise, continuing to use such reticle in a subsequent photolithography process.

7. The method of claim 1, further comprising removing a global offset from the difference intensity map.

8. The method of claim 7, wherein the difference intensity map comprises differently colored areas that correspond to different areas of the reticle that resulted in different changes in average intensity measurements between the first and second inspections.

9. The method of claim 1, wherein the difference intensity map is generated to be normalized to a zero average.

10. The method of claim 1, wherein the difference intensity map is generated based on both reflected and transmitted light that is collected during the first and second inspections.

11. The method of claim 1, further comprising:
after the reticle has been cleaned, using the optical reticle inspection tool during a third inspection to direct an incident beam towards each patch area set of the reticle and then, in response to the incident beam, measure a plurality of second reference intensity measurements from a plurality of sub-areas of each patch area set;
determining a second reference average by averaging the plurality of second reference intensity measurements from the plurality of sub-areas of each patch area set;
after using the reticle in a second plurality of photolithography processes, using the optical reticle inspection tool during a fourth inspection to direct an incident beam towards each patch area set and then in response to the incident beam measure a plurality of second test intensity measurements from a plurality of sub-areas of each patch area set;
determining a second test average by averaging the plurality of second test intensity measurements from the plurality of sub-areas of each patch area set, wherein a same setup recipe for the optical reticle inspection tool is used for both the third and fourth inspections so that the second test average for each patch area set has a same location and aligns with the second reference average for such same patch area set of the reticle; and
for each patch area set, determining a second difference between each aligned second reference and test average and representing and displaying on a display such second difference visually in a second difference intensity map so that different intensity difference values or ranges are shown in different visual ways.

12. The method of claim 1, wherein the first inspection is performed prior to using the reticle in any photolithography process after such reticle has been verified as having minimal degradation.

13. The method of claim 1, further comprising determining a global CD change based on a global offset in the difference intensity map.

14. The method of claim 1, wherein the difference intensity map is generated to account for pattern density dependencies by scaling the intensity differences by the amount of edge pixels within each set of one or more patch areas.

15. An inspection system for inspecting a photolithographic reticle, the system comprising:
an illumination source for generating an incident light beam;
illumination optics for directing the incident light beam towards the reticle;
collection optics for directing reflected and/or transmitted light from the reticle, in response to the incident light, onto one or more sensors;
one or more sensors for receiving the reflected and/or transmitted light from the reticle and generating a plurality of intensity values based on such reflected and/or transmitted light;
a display; and
at least one memory and at least one processor that are configured to perform the following operations:
during a first time period and prior to using a reticle in any photolithography process for fabricating semiconductor wafers, using the illumination source and illumination optics during a first inspection to direct an incident beam towards each of a plurality of sets of one or more patch areas of the reticle and then using the collection optics and one or more sensors, in response to the incident beam, measure a plurality of reference intensity measurements from a plurality of sub-areas of each patch area, wherein the patch area sets substantially comprise the entire active areas of the reticle;
for measurements obtained during the first time period, determining a reference average for each patch area set by averaging the plurality of reference intensity measurements from the plurality of sub-areas of the patch area set;
after using the reticle in a plurality of photolithography processes for fabricating semiconductor wafers and during a second time period that differs from the first time period, using the optical reticle inspection tool during a second inspection to direct an incident beam towards each of the patch area sets and then in response to the incident beam measure a plurality of test intensity measurements from a plurality of sub-areas of each patch area set;

for measurements obtained during the second time period, determining a test average for each patch area set by averaging the plurality of test intensity measurements from the plurality of sub-areas of the patch area set, wherein a same setup recipe for the optical reticle inspection tool is used for both the first and second inspections so that the test average for each patch area set has a same location and aligns with the reference average for such same patch area set of the reticle; and;

for each of the patch area sets, determining an intensity difference between each aligned reference average, which was determined for each patch area set during the first time period, and test average, which was determined for each patch area set during the second time period, and representing and displaying on the display such intensity difference visually in a difference intensity map for qualifying the reticle for further use so that different values or ranges for the intensity differences are shown in different visual ways and such difference intensity map shows relative positions of the intensity differences for the patch area sets comprising the entire active areas of the reticle to display changes in intensity across the reticle during the differing first and second time periods.

16. The system of claim 15, wherein the first and second inspections are performed while a pellicle is mounted on the reticle and the difference intensity map indicates whether a pellicle of the reticle has degraded over time more than a predefined level.

17. The system of claim 15, wherein the difference intensity map indicates that the reticle has degraded in a spatially radial pattern over time more than a predefined level.

18. The system of claim 15, wherein each of the sets of one or more patch areas consist of a single patch area.

19. The system of claim 15, wherein each of the sets of one or more patch areas include two or more of the patch areas.

20. The system of claim 15, wherein the at least one memory and at least one processor are further configured to remove a global offset from the difference intensity map.

21. The system of claim 20, wherein the difference intensity map comprises differently colored areas that correspond to different areas of the reticle that resulted in different changes in average intensity measurements between the first and second inspections.

22. The system of claim 15, wherein the difference intensity map is generated to be normalized to a zero average.

23. The system of claim 15, wherein the difference intensity map is generated based on both reflected and transmitted light that is collected during the first and second inspections.

24. The system of claim 15, wherein the at least one memory and at least one processor are further configured for:

after the reticle has been cleaned, using the optical reticle inspection tool during a third inspection to direct an incident beam towards each patch area set of the reticle and then, in response to the incident beam, measure a plurality of second reference intensity measurements from a plurality of sub-areas of each patch area set;

determining a second reference average by averaging the plurality of second reference intensity measurements from the plurality of sub-areas of each patch area set;

after using the reticle in a second plurality of photolithography processes, using the optical reticle inspection tool during a fourth inspection to direct an incident beam towards each patch area set and then in response to the incident beam measure a plurality of second test intensity measurements from a plurality of sub-areas of each patch area set;

determining a second test average by averaging the plurality of second test intensity measurements from the plurality of sub-areas of each patch area set, wherein a same setup recipe for the optical reticle inspection tool is used for both the third and fourth inspections so that the second test average for each patch area set has a same location and aligns with the second reference average for such same patch area set of the reticle; and for each of the sets of one or more patch areas, determining a second difference between each aligned second reference and test average and representing and displaying on a display such second difference visually in a second difference intensity map so that different intensity difference values or ranges are shown in different visual ways.

25. The system of claim 15, wherein the first inspection is performed prior to using the reticle in any photolithography process after such reticle has been verified as having minimal degradation.

26. The system of claim 15, wherein the at least one memory and at least one processor are further configured to determine a global CD change based on a global offset in the difference intensity map.

27. The system of claim 15, wherein the difference intensity map is generated to account for pattern density dependencies by scaling the intensity differences by the amount of edge pixels within each set of one or more patch areas.

28. A computer readable medium having instruction stored thereon for performing the following operations:

during a first time period and prior to using a reticle in any photolithography process for fabricating semiconductor wafers, using an optical reticle inspection tool during a first inspection to direct an incident beam towards each of a plurality of sets of one or more patch areas of the reticle and then, in response to the incident beam, measure a plurality of reference intensity measurements from a plurality of sub-areas of each patch area, wherein the patch area sets substantially comprise the entire active areas of the reticle;

for measurements obtained during the first time period, determining a reference average for each patch area set by averaging the plurality of reference intensity measurements from the plurality of sub-areas of the patch area set;

after using the reticle in a plurality of photolithography processes for fabricating semiconductor wafers and during a second time period that differs from the first time period, using the optical reticle inspection tool during a second inspection to direct an incident beam towards each of the patch area sets and then in response to the incident beam measure a plurality of test intensity measurements from a plurality of sub-areas of each patch area set;

for measurements obtained during the second time period, determining a test average for each patch area set by averaging the plurality of test intensity measurements from the plurality of sub-areas of the patch area set, wherein a same setup recipe for the optical reticle inspection tool is used for both the first and second inspections so that the test average for each patch area set has a same location and aligns with the reference average for such same patch area set of the reticle; and for each of the patch area sets, determining an intensity difference between each aligned reference average, which was determined for each patch area set during the first time period, and test average, which was determined for each patch area set during the second time period, and representing and displaying on a display such intensity difference visually in a difference intensity map for qualifying the reticle for further use so that different values or ranges for the intensity differences are shown in different visual ways and such difference intensity map shows relative positions of the intensity differences for the patch area sets comprising the entire active areas of the reticle to display changes in intensity across the reticle during the differing first and second time periods.

* * * * *